US012778981B2

(12) United States Patent
Gomez et al.

(10) Patent No.: US 12,778,981 B2
(45) Date of Patent: Nov. 3, 2026

(54) LIPID COMPOSITION CONTAINING MICRONUTRIENTS FOR THE PREVENTION AND/OR TREATMENT OF METABOLIC DISEASES

(71) Applicant: ALIANZA TEAM INTERNATIONAL S.A., Bogota (CO)

(72) Inventors: Luisa Fernanda Gomez, Bogota (CO); Eddy Carolina Betancourt, Bogota (CO); Camilo Andres Castro, Bogota (CO); Carlos Alvarez, Bogota (CO); Daniel Colmenares, Bogota (CO)

(73) Assignee: ALIANZA TEAM INTERNATIONAL S.A., Bogota (CO)

( * ) Notice: Subject to any disclaimer, the term of this patent is extended or adjusted under 35 U.S.C. 154(b) by 1068 days.

(21) Appl. No.: 17/286,352

(22) PCT Filed: Aug. 9, 2019

(86) PCT No.: PCT/IB2019/056800
§ 371 (c)(1),
(2) Date: Apr. 16, 2021

(87) PCT Pub. No.: WO2020/079497
PCT Pub. Date: Apr. 23, 2020

(65) Prior Publication Data

US 2021/0353669 A1 Nov. 18, 2021

Related U.S. Application Data

(60) Provisional application No. 62/746,991, filed on Oct. 17, 2018.

(51) Int. Cl.

| | |
|---|---|
| ***A61K 33/24*** | (2019.01) |
| ***A61K 31/201*** | (2006.01) |
| ***A61K 31/202*** | (2006.01) |
| ***A61K 31/4402*** | (2006.01) |
| ***A61K 31/575*** | (2006.01) |
| ***A61K 36/15*** | (2006.01) |
| ***A61K 36/185*** | (2006.01) |
| ***A61K 36/31*** | (2006.01) |
| ***A61K 36/53*** | (2006.01) |
| ***A61K 36/889*** | (2006.01) |
| ***A61K 36/899*** | (2006.01) |
| ***A61K 36/9066*** | (2006.01) |

(52) U.S. Cl.
CPC ............ *A61K 33/24* (2013.01); *A61K 31/201* (2013.01); *A61K 31/202* (2013.01); *A61K 31/4402* (2013.01); *A61K 31/575* (2013.01); *A61K 36/15* (2013.01); *A61K 36/185* (2013.01); *A61K 36/31* (2013.01); *A61K 36/53* (2013.01); *A61K 36/889* (2013.01); *A61K 36/899* (2013.01); *A61K 36/9066* (2013.01)

(58) Field of Classification Search
CPC .... A61K 33/24; A61K 31/201; A61K 31/202; A61K 31/4402; A61K 31/575; A61K 36/15; A61K 36/185; A61K 36/31; A61K 36/53; A61K 36/889; A61K 36/899; A61K 36/9066; A61K 31/12; A61K 45/06; A23L 33/11; A23L 33/12; A23L 33/16; A23L 33/105; A61P 3/00
See application file for complete search history.

(56) References Cited

U.S. PATENT DOCUMENTS

| | | | | |
|---|---|---|---|---|
| 11,865,121 | B2 * | 1/2024 | Komorowski | A61K 9/14 |
| 2001/0016580 | A1 * | 8/2001 | Harpe | A61K 45/06 514/188 |
| 2003/0054082 | A1 * | 3/2003 | Koike | A23L 33/11 426/601 |
| 2008/0146664 | A1 * | 6/2008 | Okuyama | A61P 1/16 424/776 |
| 2012/0251621 | A1 * | 10/2012 | Reising | A61P 3/00 424/94.1 |
| 2014/0170128 | A1 * | 6/2014 | Pasupuleti | A61K 38/28 424/94.1 |
| 2018/0271131 | A1 * | 9/2018 | Moreno Egea | A61P 21/00 |

FOREIGN PATENT DOCUMENTS

| | | |
|---|---|---|
| JP | 2008031177 | * 2/2008 |
| WO | WO 2013086243 | * 9/2013 |
| WO | WO 2016/189345 | * 12/2016 |

OTHER PUBLICATIONS

ClinicalTrials.gov "Evaluation of the Impact of a Nutritional Supplement Made of Vegetable Oils in People at Risk of Diabetes" 2018.*
Balk et al. "Effect of Chromium Supplementation on Glucose Metabolism and Lipids: A systemic review of randomized controlled trials" 2007.*

* cited by examiner

*Primary Examiner* — Jessica Worsham
(74) *Attorney, Agent, or Firm* — Patenting Consulting Group; Roberto J Rios

(57) ABSTRACT

The present invention relates to the field of nutritional products used as non-pharmacological therapy alternatives for the prevention and/or treatment of metabolic disorders. The lipid-based composition with micronutrients described herein comprises at least 98 weight percent of lipids of natural origin, which include at least one phytosterol and one or more unsaturated fatty acids, and in addition, at least one natural antioxidant, one or more polyphenols of plant origin and at least one chromium compound, this composition achieves positive effects in different metabolic parameters in subjects with metabolic alterations and/or cardiovascular risk.

11 Claims, 8 Drawing Sheets

LIPID COMPOSITION CONTAINING MICRONUTRIENTS FOR THE PREVENTION AND/OR TREATMENT OF METABOLIC DISEASES

BACKGROUND AND FIELD OF THE INVENTION

Chronic non-communicable diseases (NCDs) represent 63% of deaths worldwide, of which 80% occur in low- and middle-income countries. Said NCDs include the metabolic syndrome, which encompasses a set of cardiovascular risk factors characterized by alterations in glucose and lipid metabolism, which are related to insulin resistance and, in turn, promote the future development of Type II diabetes mellitus (DM2).

Type II diabetes is defined by high levels of glucose in the blood and is related to an absolute or relative insufficiency in the secretion or action of insulin. Also, this disease is associated with modifiable risk factors, such as obesity or overweight, physical inactivity and hypercaloric and low nutritional value diets. The development of diabetes is preceded by a set of disorders known as pre-diabetes, a term that includes intolerance to carbohydrates and the alteration of fasting blood glucose. The prevalence of pre-diabetes is in frank increase and the public health efforts made to contain this epidemic have had a very limited impact.

As part of the alternatives explored for the management of said metabolic alterations, non-pharmacological therapies have been developed that include the use of nutraceuticals, foods or supplements with the ability to favorably modify the course of the disease or to effectively impact the factors risky.

This is how a wide variety of glycemic control alternatives are currently available in the market, such as Glucerna®, Ensure® Diabetics care, Nutren Diabetes®, Nutren Diabetes®, Boost® Glucose Control, Glytrol®, Diabetishield®, Gluvid®, Enterex® diabetic, Resource diabetic, Diabeticsource®, NAT100® diabetic, Fontactiv® Diabest; however, these alternatives are based on the use of carbohydrates with low glycemic index to achieve a favorable metabolic effect.

In this way, the formulation of the commercial products described above includes slow release and absorption carbohydrates, as well as a variety of additional nutrients, such as insoluble or soluble fibers, concentrates or mixtures of proteins from milk and/or soy, vegetable oils, low caloric sweeteners such as Acelsufame K or sucralose, antioxidants, vitamins and minerals. Particularly, the most commonly used carbohydrates in such formulations are modified maltodextrin, fructo-oligosaccharides (sc-FOS), inulin, sucromaltose, and tapioca dextrin, as well as mixtures thereof.

However, these approaches ignore the contribution of dietary lipids, which are of high interest in the field of metabolic diseases because they influence glucose metabolism, enzymatic activity, insulin signaling and gene expression. Additionally, it has been proposed that lipid consumption is part of a dietary lifestyle strategy to prevent or treat type II diabetes and decrease cardiovascular risk by reducing the proportion of low density lipoproteins (LDL) and triglycerides.

Taking into account the above, alternatives that include said nutrients have been proposed. Thus, patent document U.S. Pat. No. 5,470,839 discloses nutritional compositions directed to patients with diabetes, which include, in addition to starch with high content of amylose, a source of protein and soluble dietary fiber, a source of fat comprising medium chain triglycerides and a high percentage of monounsaturated fats. Thus, an enteral formulation rich in fats and low in carbohydrates is provided in this document. However, this alternative continues to depend on the use of low absorption carbohydrates to achieve a reduction in the glycemic index.

Thus, it is evident that, although currently there are products on the market offered as complementary treatments to the use of drugs for patients with DM2 or in a pre-diabetes state, said products offer solutions based solely on glycemic index reduction by means of the consumption of slow absorption carbohydrates. Additionally, it is important to point out that these solutions are not balanced in nutritional terms and therefore do not act integrally in the regulation of pathophysiological factors that are related to the state of hyperglycemia. Also, in some cases, the caloric intake of these commercial products may exceed the recommended daily values, so they could act as promoters of obesity, thus generating an adverse effect.

In this sense, it is evident that the need persists to provide compositions that act as adjuvants in the non-pharmacological approach of patients with diabetes and/or pre-diabetes, which act directly in the key pathophysiological mechanisms of type II diabetes mellitus.

GENERAL DESCRIPTION OF THE INVENTION

The present invention relates to lipid nutritional compositions comprising a mixture of bioactive ingredients (lipids and micronutrients), aimed at individuals at risk of developing diabetes, with pre-diabetes, obesity and/or overweight, glucose intolerance and/or insulin resistance.

In one embodiment, the lipid-based composition with micronutrients of the invention includes at least 98 weight percent lipids. In other embodiments, the lipid-based composition with micronutrients of the invention may comprise a vegetable oil, wherein the vegetable oil preferably comprises sunflower oil, soybean oil, canola oil, olive oil, linseed oil or combinations thereof. In still other embodiments, the lipid-based composition with micronutrients of the invention includes water-soluble and fat-soluble micronutrients.

In a particular embodiment, the lipid-based composition with micronutrients of the invention can be prepared from natural sources including, but not limited to, sea buckthorn oil, pine oil, pomegranate oil, plant phytosterols, turmeric, natural antioxidants derived from rosemary extracts, rice extracts, coconut extracts, canola oil, and combinations thereof. On the other hand, the lipid-based composition of the invention includes at least one chromium compound.

In a particular embodiment, the lipid-based composition with micronutrients of the invention comprises one or more phytosterols. In yet another embodiment, the composition comprises at least one unsaturated fatty acid. In a further embodiment, the composition comprises at least one natural antioxidant. In another embodiment, the composition comprises one or more polyphenols of plant origin. In a further embodiment, the composition comprises one or more chromium compounds.

In another embodiment, the invention relates to a food product comprising, in addition to the lipid-based composition with micronutrients described in the preceding paragraphs, at least one excipient selected from a group including, but not limited to, thickeners, texturizers, colorants, acidulants, and/or natural flavorings.

In one embodiment, the lipid-based composition with micronutrients of the invention can be consumed directly. In another embodiment, the lipid-based composition with micronutrients of the invention can be incorporated into different matrices to be used in the food industry, such as powdered or ready-to-drink (RTD) drinks, cookies, bread products, snacks, as well as drinks and dairy products.

In a further embodiment, the lipid-based composition with micronutrients of the invention is able to improve pathophysiological phenomena associated with the development of diabetes and its complications, achieving effects in different metabolic parameters in people with metabolic disorders and/or cardiovascular risk.

In another embodiment, the lipid-based composition with micronutrients of the invention directly influences key pathophysiological mechanisms of type II diabetes mellitus, such as reduction of blood glucose, sensitization and secretion of insulin in muscle and adipose tissue, decrease of chronic low-grade inflammation, reduction of hepatobiliary and liver damage.

In other embodiments, the present invention relates to a method for treating individuals at risk of developing diabetes, who exhibit pre-diabetes, diabetes, obesity and/or overweight, glucose intolerance and/or insulin resistance, wherein the method comprises: orally administering to the individual an effective amount per day of a composition according to any of the embodiments of the invention.

DETAILED DESCRIPTION OF THE INVENTION

Figure 1:
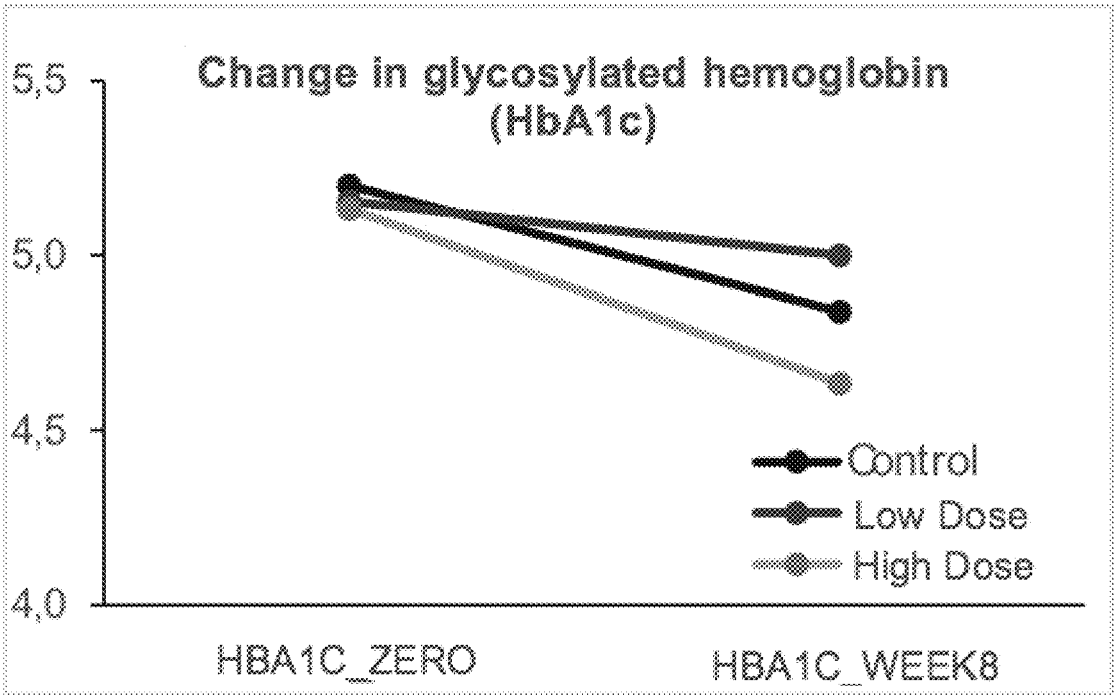
FIG. 1 shows the results of a glycosylated hemoglobin levels (HbA1c) study.

Detailed embodiments of the present invention are described below in the present document; however, it should be understood that they are merely illustrative and can be incorporated in various forms. In addition, each of the examples given in relation to the various embodiments of the invention are intended to be illustrative and not restrictive.

The present invention relates to a lipid-based composition with micronutrients comprising at least 98 weight percent of lipids of natural origin, including at least one phytosterol and one or more unsaturated fatty acids, wherein the composition comprises in addition to at least one natural antioxidant, one or more polyphenols of plant origin and at least one chromium compound.

In one embodiment, the lipid-based composition with micronutrients of the invention can be prepared from natural sources including, but not limited to, buckthorn oil, pine oil, pomegranate oil, plant phytosterols, turmeric, natural antioxidants derived from rosemary extracts, rice extracts, coconut extracts, canola oil, and combinations thereof. Also, the composition includes a chromium compound.

In one embodiment, the lipid-based composition with micronutrients of the invention comprises at least one phytosterol in a range of between 20 to 30 weight percent. In still other embodiments, the composition includes at least one phytosterol in a range of between 23.5 to 24.5 weight percent. In yet another embodiment, the phytosterol is selected from a group that includes, but is not limited to, 13-sitosterol, ergosterol, stigmasterol and campesterol. In a preferred embodiment the phytosterol comprises campesterol.

In one embodiment, the lipid-based composition with micronutrients of the invention includes one or more unsaturated fatty acids in a range of between 70 to 90 weight percent. In particular embodiments, the composition includes one or more unsaturated fatty acids in a range of between 73 to 80 weight percent. In a preferred embodiment the unsaturated fatty acids are selected from a group comprising pinolenic acid, palmitoleic acid, punicic acid, conjugated linoleic acid (CLA), and linolenic acid isomers (C18:3) such as alpha-potenic acid, alpha-eleostearic and catalpic acid. In a preferred embodiment, the lipid-based composition with micronutrients of the invention includes a mixture of pinolenic acid, palmitoleic acid and punicic acid.

In a preferred embodiment, the lipid-based composition with micronutrients of the invention includes from 20 to 30 weight percent of pinolenic acid, 30 to 40 weight percent of palmitoleic acid and 10 to 20 weight percent of punicic acid.

In one embodiment, the lipid-based composition with micronutrients of the invention comprises at least one natural antioxidant in a range of between 0.3 to 3.0 weight percent. In other embodiments, the composition includes at least one natural antioxidant in a range of between 0.5 to 1.5 weight percent. In yet another embodiment, the natural antioxidant is selected from a group comprising, but not limited to, rosemary extracts derivatives, rice extracts derivatives, coconut extracts derivatives, canola oil derivatives and mixtures thereof.

In a further embodiment, the lipid-based composition with micronutrients of the invention comprises one or more polyphenols of plant origin in a range of between 0.5 to 5 weight percent. In other embodiments, the lipid-based composition with micronutrients of the invention includes one or more polyphenols of plant origin in a range of between 0.5 to 2.0 weight percent. In a preferred embodiment, polyphenols of plant origin include a mixture of curcuminoids.

In one embodiment, the lipid-based composition with micronutrients of the invention comprises at least one chromium compound in a range of between 0.01 to 0.1 weight percent. In one embodiment, the chromium compound is a chromium compound used in the food industry. In another embodiment, the chromium compound is an organic chromium compound. In yet another embodiment, the chromium compound is an inorganic chromium compound. In yet other embodiments, the chromium compound is selected from the group including, but not limited to, chromium picolinate, chromium polynicotinate, chromium chloride, or any mixture thereof.

In one embodiment, the lipid-based composition with micronutrients of the invention is in a form suitable for direct consumption, such as in the encapsulated form, liquid emulsion, microencapsulated powder or suspension.

In another embodiment, the lipid-based composition with micronutrients of the invention can be incorporated into different matrices commonly used in the food industry, such as powdered or ready-to-drink beverages, shakes, creams, biscuits, bakery products, snacks, drinks and dairy products.

In some embodiments, the lipid-based composition with micronutrients of the invention is provided as a gel, dispersion, suspension or solution in oil. In another embodiment, the lipid-based composition with micronutrients of the invention of the invention can be suspended in refined vegetable oils including but not limited to olive oil, sunflower oil, soybean oil, canola oil, medium chain triglycerides (MCTs), palm kernel, linseed oil or mixtures thereof.

In some embodiments, the lipid-based composition with micronutrients of the invention has effects on different metabolic parameters in persons with metabolic disorders and/or cardiovascular risk and serves as an adjunct to the approach of patients with diabetes and/or pre-diabetes.

In another embodiment the invention provides a method for treating individuals at risk of developing diabetes or exhibiting pre-diabetes, diabetes, obesity and/or overweight, glucose intolerance and/or insulin resistance; wherein the method comprises orally administering to the individual in need thereof an effective amount per day of a composition according to any of the modalities described herein.

In a further embodiment, the invention relates to a method for treating individuals at risk of developing diabetes or exhibiting pre-diabetes, diabetes, obesity and/or overweight, glucose intolerance and/or insulin resistance; wherein the method comprises orally administering to the individual in need thereof an effective amount per day of a composition that includes at least 98 weight percent of lipids of natural origin, including at least one phytosterol and one or more unsaturated fatty acids, wherein the composition further includes at least one natural antioxidant, one or more polyphenols of plant origin and at least one chromium compound.

In the embodiments, the effective amount of the composition is based, at least in part, on the weight of the human being who needs it.

In yet other embodiments, the effective amount is between 0.5 g to 2 g per dose. In other embodiments, the effective amount includes 0.82 g per dose. In other embodiments, the effective amount includes 1.64 g per dose.

EXAMPLES

The following examples are intended to illustrate the invention and should not be interpreted as limiting the invention in any way.

In order to evaluate the effect of an embodiment of the lipid-based composition according to invention, a pilot study was designed as a clinical trial, on the sensitivity to insulin, cardiovascular risk factors, composition and body weight in people with risk of diabetes. Parameters of the study: three-arm randomized controlled, with masking, of 8-weeks duration. This study was registered under NCT code 03512665 at www.clinicaltrials.gov, and its content is incorporated in its entirety as a reference.

The conditions and main results of said study are described below:

Participants: Adults who are at risk of diabetes were included. According to the following inclusion and exclusion criteria:

Inclusion criteria:

- Over 18 years of both sexes
- Risk of type 2 diabetes (DM2) due to a history of DM2 in a first-degree relative and/or a body mass index greater than or equal to 25 Kg/m$^2$ and/or a FinnRisc score greater than 12.
- Clear desire to participate in the study, and informed consent.
- Successfully demonstrate a 80% or more of adhesion during the induction phase of a week of duration.

Exclusion Criteria:

- To be in an active and systematic program of weight loss.
- Known hypersensitivity to any of the components present in the supplement
- Gastrointestinal problems that negatively affect adherence to the study
- Known complications of diabetes or hypertension: Cardiopathy, nephropathy, retinopathy, cerebrovascular disease, diabetic foot or painful neuropathy.

Sample size: 8 participants per group (Control, low dose and high dose) The statistical significance is therefore less than or equal to 0.1

Study Groups:

- BP Group: 1 daily dose of 7 mL of refined sunflower oil (Control).
- SDB Group: 1 daily dose composed of 3.5 mL of the composition according to the invention and 3.5 mL of sunflower oil (low dose)
- SDA Group: 1 daily dose of 7 mL of a composition as previously described (High dose).

Follow-up: A one-week induction phase is carried out to evaluate adherence to the intake of the assigned composition Measurements:

Tests performed for the three study groups at the beginning and at the end of the follow-up (week 0 and week 8):

- Anthropometric assessment, blood pressure and body composition.
- Physical activity by iPAQ.
- Basal consumption. Total calories, carbohydrates, proteins, total lipids, saturated fatty acids, monounsaturated, polyunsaturated and trans, EPA, DHA, dietary cholesterol, and 15 micronutrients: Calcium, iron, sodium, phosphorus, zinc, potassium, vitamin A, vitamin E, vitamin K, vitamin D, thiamine, riboflavin, niacin, vitamin C and folate.
- Insulin sensitivity: oral glucose tolerance test with glycemia and insulinemia, determination of insulin sensitivity and resistance indexes, glycosylated hemoglobin
- Carbohydrate and lipid metabolism (lipid profile, triglycerides, total cholesterol, LDL, HDL); hepatic (liver transaminases, gamma-glutamyl transferase) and renal function (creatininemia, urinary albumin excretion) and low-grade inflammation (C-reactive protein) tests.
- Gastrointestinal hormones for regulating appetite and metabolic rate:
  - GLP-1
  - Ghrelin
  - Glucagon
  - These hormones were measured at minute zero (preload) and at 120 minutes post glucose load, both at the beginning and at the end of the study.

Adipokines produced by adipose tissue and responsible for regulating body metabolism:

Leptin

Adiponectin

Resistin

These hormones were measured at the beginning and at the end of the follow-up (week zero and week 8).

Myochines that influence the metabolism in muscle and other tissues:

Irisin

Mionectin

FGF-21

These hormones were measured at the beginning and at the end of the follow-up (week zero and week 8).

Determination of adverse events; for the baseline visit, the follow-up and the final visit.

Tests performed on the three study groups, at the beginning, at 4 weeks and at 8 weeks of follow-up:

Change in: Weight, body mass index, body fat %, waist circumference.

Study's Results:

Study Group Baseline Characteristics:

The average age for the three groups is between 28 and 35 years. The average body mass index (BMI) is in the overweight range. Participants also have, on average, a high waist circumference and body fat percentage, and average C-reactive protein levels above 1 mg/mL, indicating chronic low-grade inflammation. The daily level of physical activity of the participants is low in the three groups, while the amount of seated time exceeds 350 minutes/week in the three groups. There are no significant differences in the baseline characteristics of the participants of the three study groups, nor in their basal intake.

Anthropometric Variables:

After the 8-week follow-up period, it was found that the intake of the lipid-based composition with micronutrients of the invention did not show significant effects on the weight, body mass index and muscle mass of the patients. However, significant differences were found in the change of waist circumference between the low dose and high dose groups versus the control group (data not shown). Thus, the lipid-based composition of the invention appears to have no adverse effects on anthropometric measurements.

Change in Indexes Associated with Glycemia, Insulin Resistance and Insulin Secretion:

According to what is shown in FIG. 1, the glycosylated hemoglobin, which reflects the accumulated glycemic levels continuously during the last 3 months, decreased in the three study groups, although more markedly in the high dose group (−0.50) than in the dose group low (−0.16) and the control group (−0.36). However, there are no significant differences between groups.

Thus, the results show that the lipid-based composition of the invention does not adversely affect the glycosylated hemoglobin and, on the contrary, a tendency to improve the chronic glycemic levels expressed by HbA1c is observed, i.e., the composition is effective in its objective principal, which is to reduce blood glucose in patients at risk of diabetes. This reduction becomes more evident in the high dose group.

Figure 2:
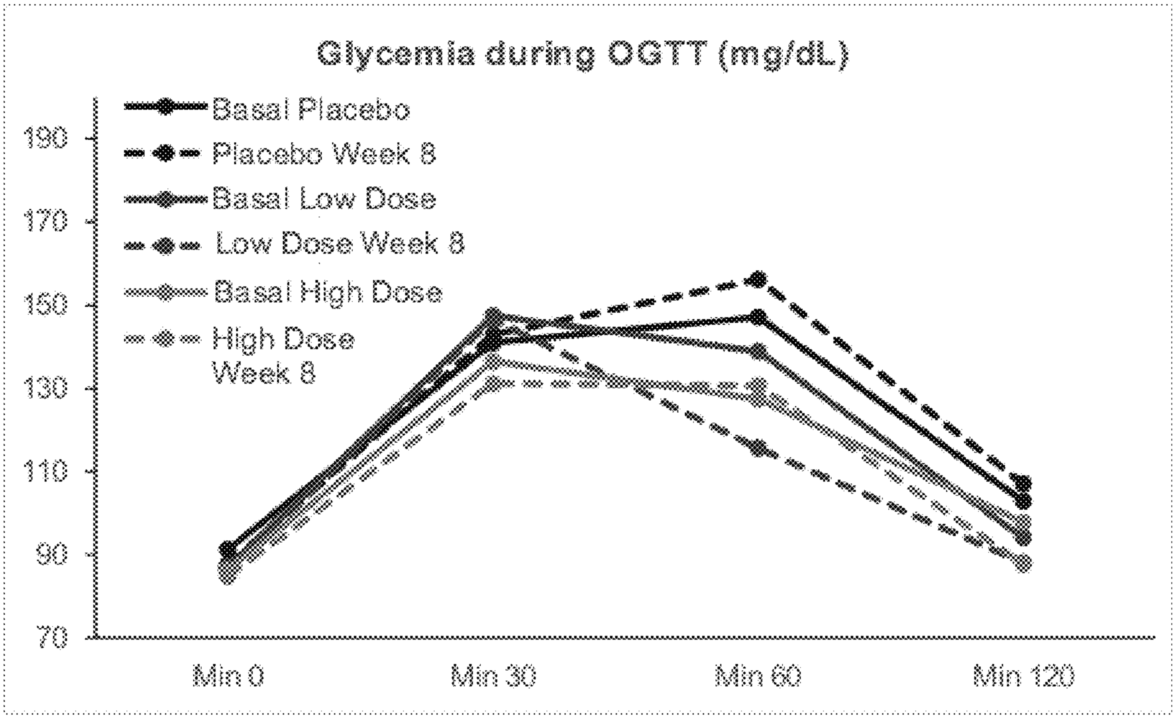
FIG. 2 shows the results of a glucose tolerance test.

On the other hand, according to FIG. 2, the administration of a lipid-based composition with micronutrients according to the invention modified the body response to the load of 75 grams of glucose in the oral glucose tolerance test.

Thus, the administration of the lipid-based composition with micronutrients of the invention has blood glucose lowering effects after 8 weeks of follow-up. Additionally, significantly lower glycemic excursions were observed at 60 and 120 minutes. This effect is highly positive and validates the effectiveness of blood glucose reduction achieved by the lipid-based composition with micronutrients of the invention.

Figure 3:
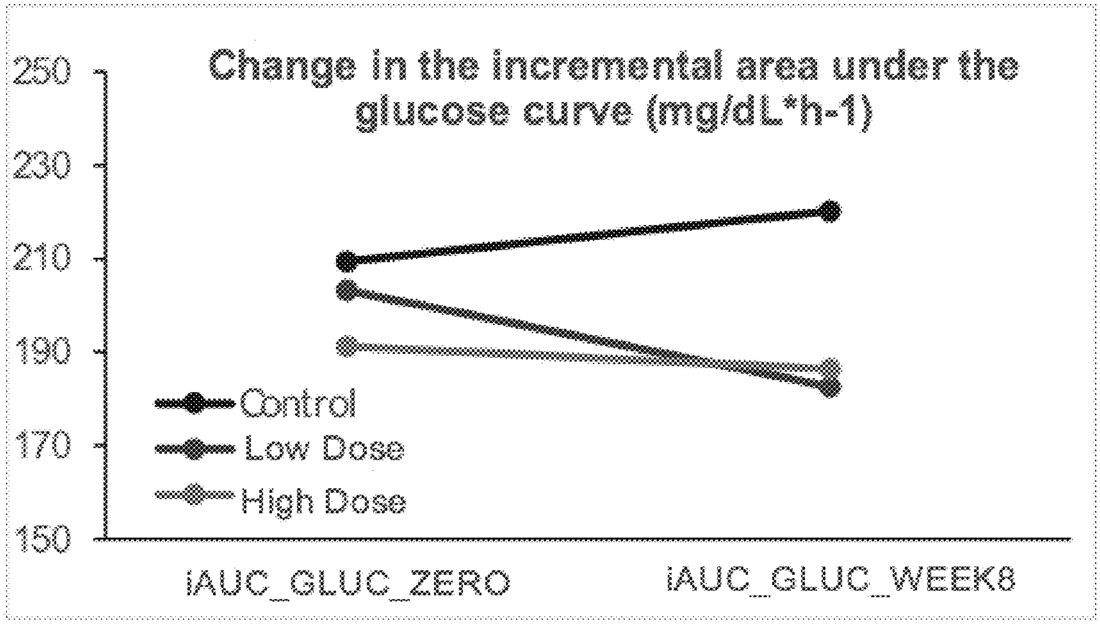
FIG. 3 shows the results an incremental area under the glucose curve study.

Also, according to FIG. 3, the incremental area under the glucose curve, which reflects the size of the glycemic excursion during an oral glucose tolerance test, was reduced with the administration of the lipid-based composition of the invention in both high and low doses, while it rose slightly in the control group. In this way, the reduction of blood glucose levels is confirmed at week 8 compared to the control group, thus verifying the effectiveness of the lipid-based composition with micronutrients in the reduction of blood glucose, and therefore showing prevention benefits in patients at risk of type II diabetes mellitus or hyperglycemia.

Figure 4:
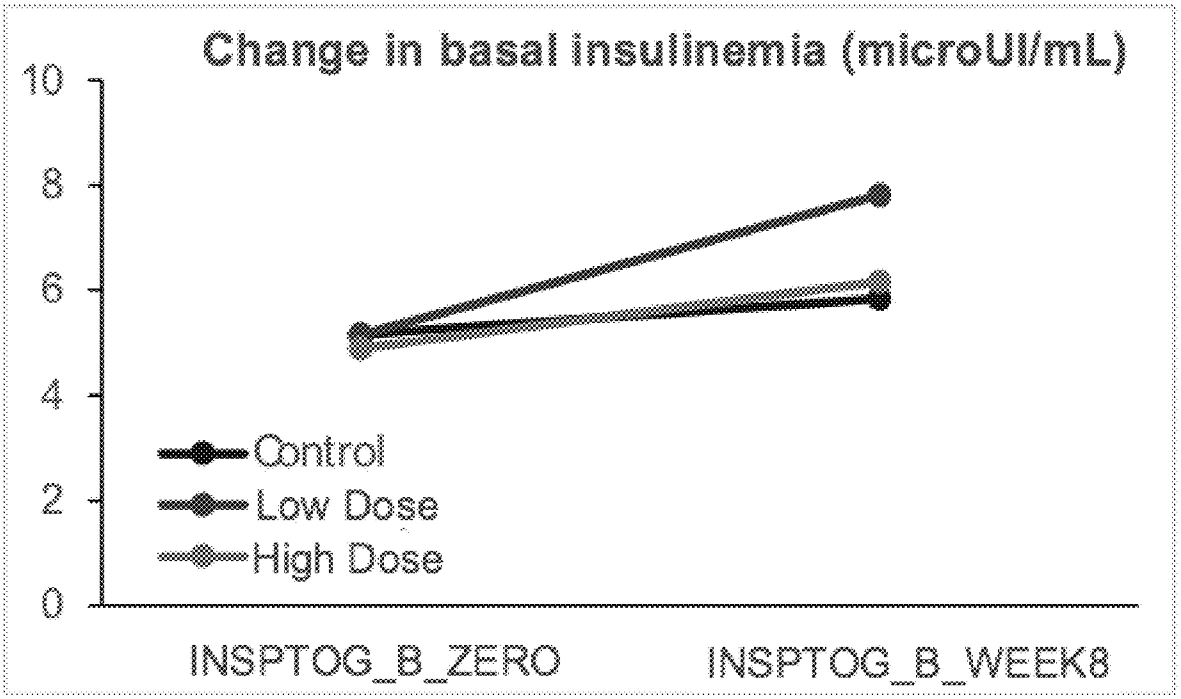
FIG. 4 shows the results of a basal insulinemia study.

In the same way, as shown in FIG. 4, basal insulinemia rose slightly in all three study groups, especially in the low dose group. These results suggest that the reduction in glucose observed at 8 weeks may be associated with a higher insulin secretion and not a resistance to it.

Figure 5:
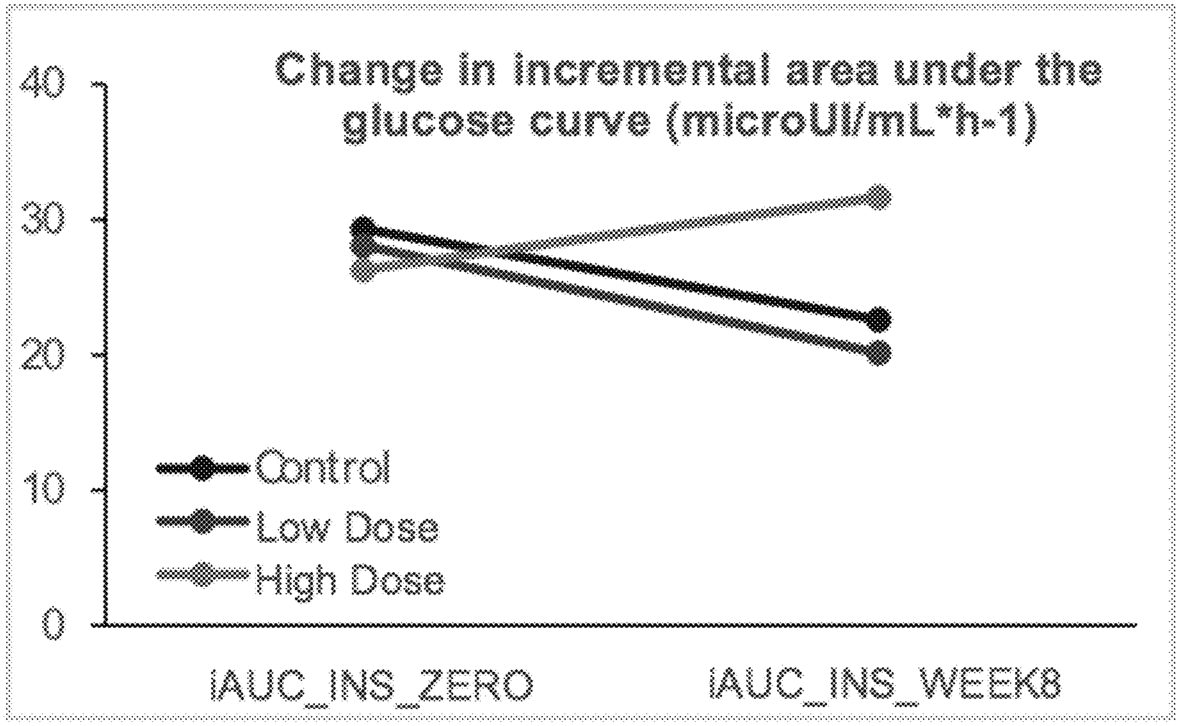
FIG. 5 shows the results of an incremental area under the insulin curve study.

Likewise, according to what is shown in FIG. 5, the measurement of insulin secretion after the glycemic challenge of the tolerance test, the incremental area under the glucose curve showed an increase in the high dose group compared to the other two groups, once again suggesting a positive effect of the lipid-based composition of the invention on insulin secretion.

Figure 6:
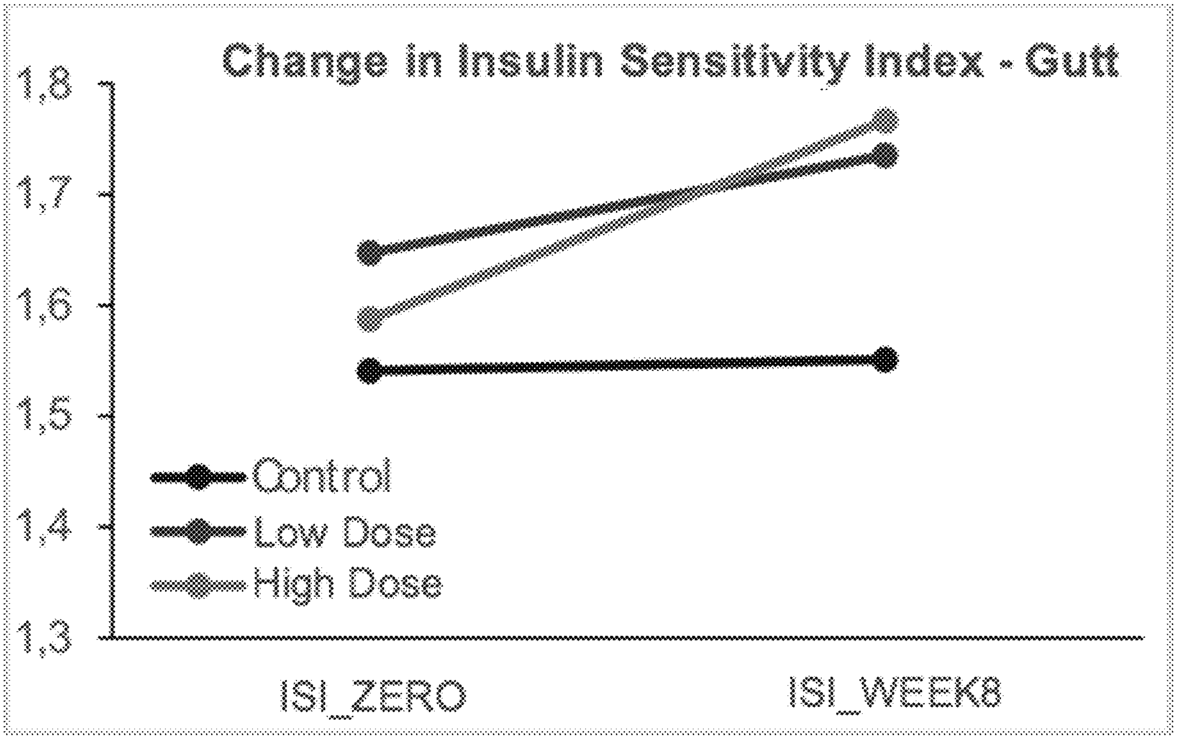
FIG. 6 shows the results of an Insulin Sensitivity Index-Gutt (ISI-Gutt) study.

Finally, FIG. 6 illustrates the results of a study of the Insulin Sensitivity Index-Gutt (ISI-Gutt), by means of which the capacity of the insulin secreted by the organism during a OGTT is quantified to stimulate the uptake of glucose in tissues peripherals Thus, ISI-Gutt is an indicator of insulin sensitivity that is not restricted to the fasting state alone and therefore allows a better measurement of insulin sensitivity.

In this way, it is evident that for both the low-dose and the high-dose groups, the ISI-Gutt improved (5.4% in the low-dose group and 10.1% in the high-dose group), whereas remained stable in the control group. These results show that the lipid-based composition of the invention has a favorable effect on the sensitization of insulin, a hormone directly associated with the uptake of glucose in adipose and muscle tissue, thus corroborating the effectiveness of the composition in the prevention of the development of diabetes.

Taking into account all of the above, it is evident that the lipid-based composition of the invention has positive and significant effects in the reduction of blood glucose, an increase in the sensitivity to insulin, as well as an improvement in the chronic glycemic levels in blood at the end of 8 weeks of follow-up.

Effects on Gastrointestinal Hormones, Adipokines and/or Myokines:

Measurements of different gastrointestinal hormones (Ghrelin, GLP-1, Glucagon), adipokines (Leptin, Adiponectin, Resitin) and myokines (FGF-21, Mionectin, Irisin) were performed to identify the metabolic mechanisms by which the lipid-based composition of the invention acts (Data not shown).

The administration of the lipid-based composition of the invention shows that there is a favorable dose-dependent effect on the secretion of the gastrointestinal hormone GLP-1, which favors the secretion of insulin. Since GLP-1 is an objective in the formulation of pharmaceutical molecules for the management of type 2 diabetes, this result shows that this metabolic pathway can also be positively affected by the intake of said composition.

Likewise, the administration of a lipid-based composition with micronutrients of the invention achieves a favorable and significant effect on the secretion of plasma leptin by adipocytes. Therefore, the intake of the lipid-based composition with micronutrients of the invention increases the efficiency of adipose tissue, metabolic expenditure and energy sufficiency.

On the other hand, the administration of a lipid-based composition of the invention achieves a favorable effect in increasing the secretion of plasma irisin in a dose-dependent manner. This significant increase in irisin shows that the lipid-based composition with micronutrients of the invention has a favorable effect on the physiology of the adipose tissue, in its particular differentiation towards 'beige' or brown adipose tissue. Likewise, the increase in this specific hormone shows the possible promotion of body thermogenesis that influences the energy and metabolic balance.

Regarding the other hormones (Ghrelin, Glucagon, Adiponectin, Resitin, FGF-21, Mionectin), their changes were not significant among the three groups, indicating that the composition of the invention seems to have no direct effect on secretion or inhibition of these hormones.

Change in Low-Grade Chronic Inflammation Indicator

Figure 7:
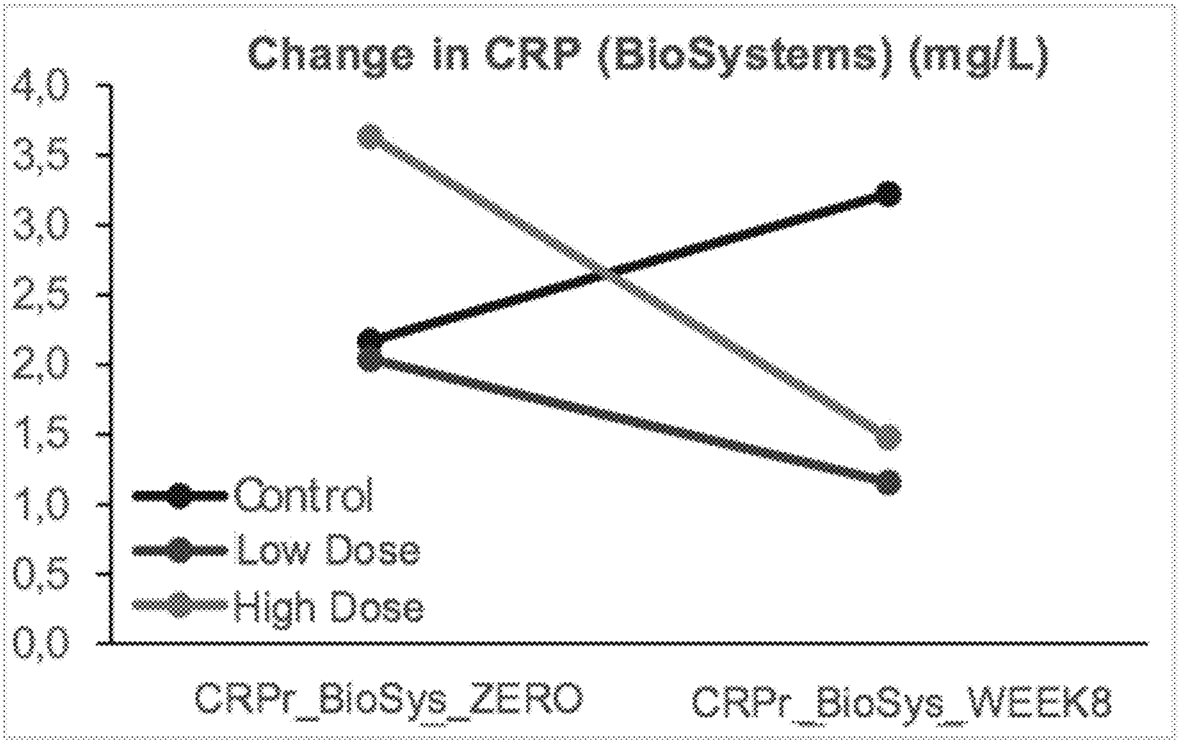
FIG. 7 shows the results of a high sensitivity C-reactive protein (hsCRP) plasma concentration study.

Also, as shown in FIG. 7, the results of C-reactive protein measurements (clinical marker or indicator of chronic low-grade inflammation) show a positive and significant effect on the reduction of chronic low-grade inflammation associated with the intake of lipid-based composition with micronutrients of the invention. The reducing effect in this biomarker suggests that, in pre-diabetes states, risk of diabetes, metabolic syndrome, the composition of lipid and micronutrients of the invention manages to reduce the risk of cardiovascular disease.

Change in Liver and Kidney Function Variables

On the other hand, in order to evaluate the hepatotoxicity and renal toxicity of the lipid-based composition of the invention, measurements of hepatic transaminases and urinary excretion of albumin were made.

Figure 8:
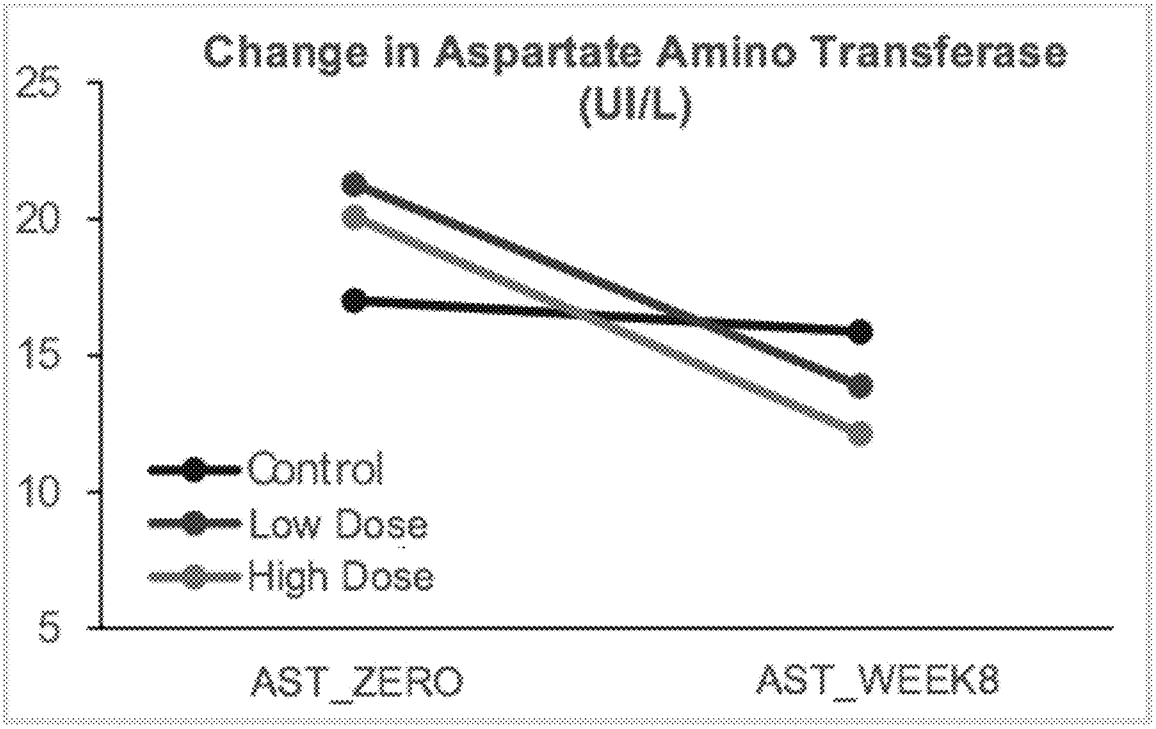
FIG. 8 shows the results of an Aspartate aminotransferase (AST) plasma levels study.

Thus, according to what is shown in FIG. 8, the levels of AST (marker of hepatocellular damage) decreased in the three groups, with the greatest decrease in the high dose group (40% on average). Hence, demonstrating a hepatoprotective and even a hepatostaurative side effect, which adds a benefit to the general condition of the metabolic syndrome that usually accompanies the stages of pre-diabetes or diabetes.

Figure 9:
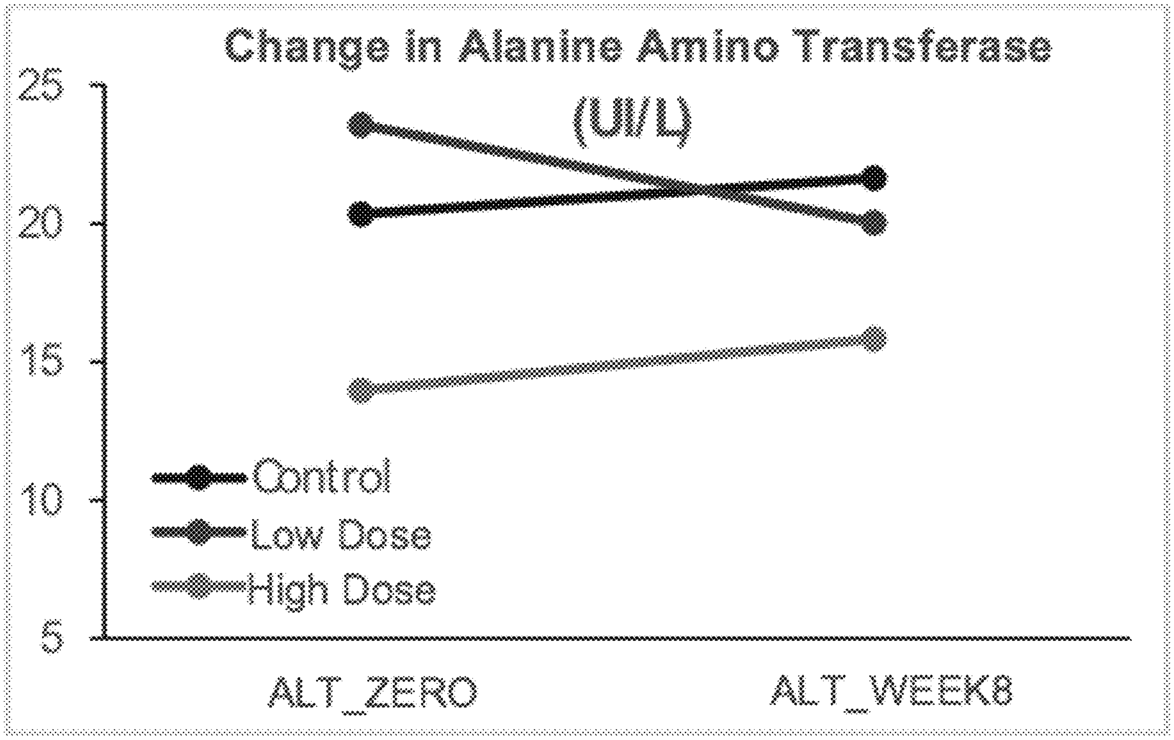
FIG. 9 shows the results of an Alanine aminotransferase (ALT) plasma levels study.

As for the ALT levels, shown in FIG. 9, the results showed a decrease only in the low dose group (16.8% on average).

Figure 10:
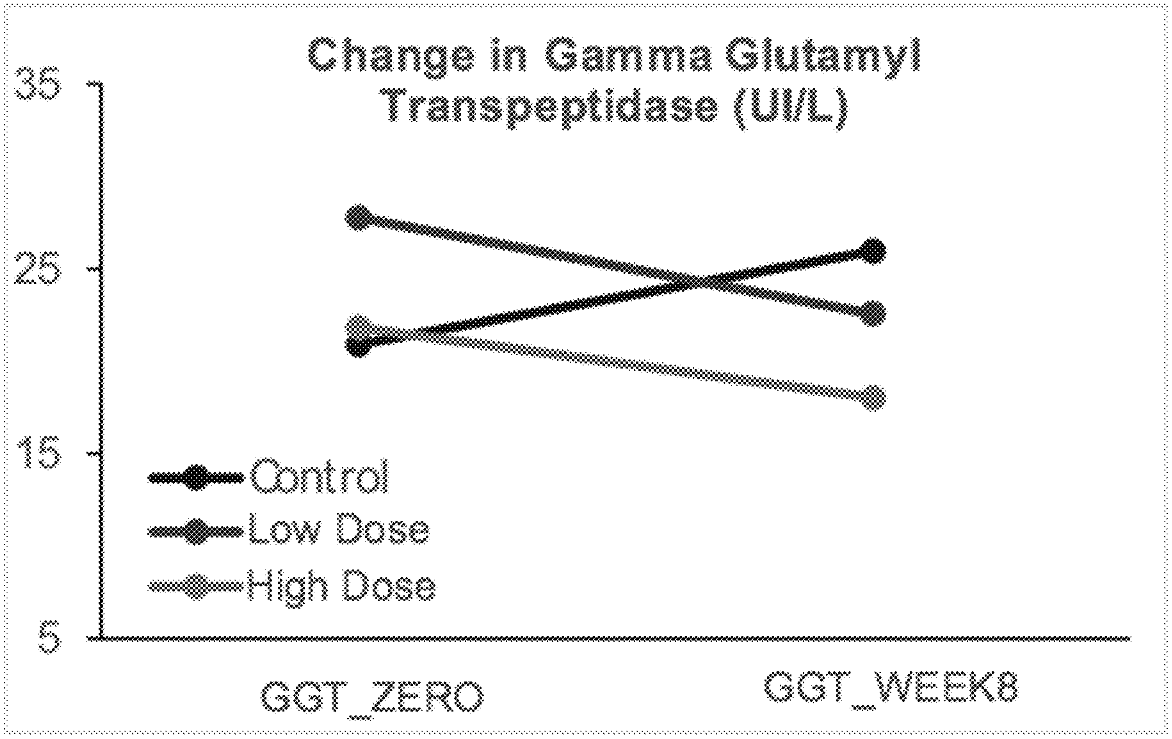
FIG. 10 shows the results of a Gamma glutamyl transpeptidase (GGT) plasma levels study.

On the other hand, as shown in FIG. 10, Gamma glutamyl transpeptidase (GGT) levels (hepatobiliary damage marker) decreased slightly in the high and low dose groups, while they increased slightly in the control group. This result suggests that the lipid-based composition of the invention offers hepatobiliary protection, usually associated with metabolic syndrome, and oxidative stress.

Figure 11:
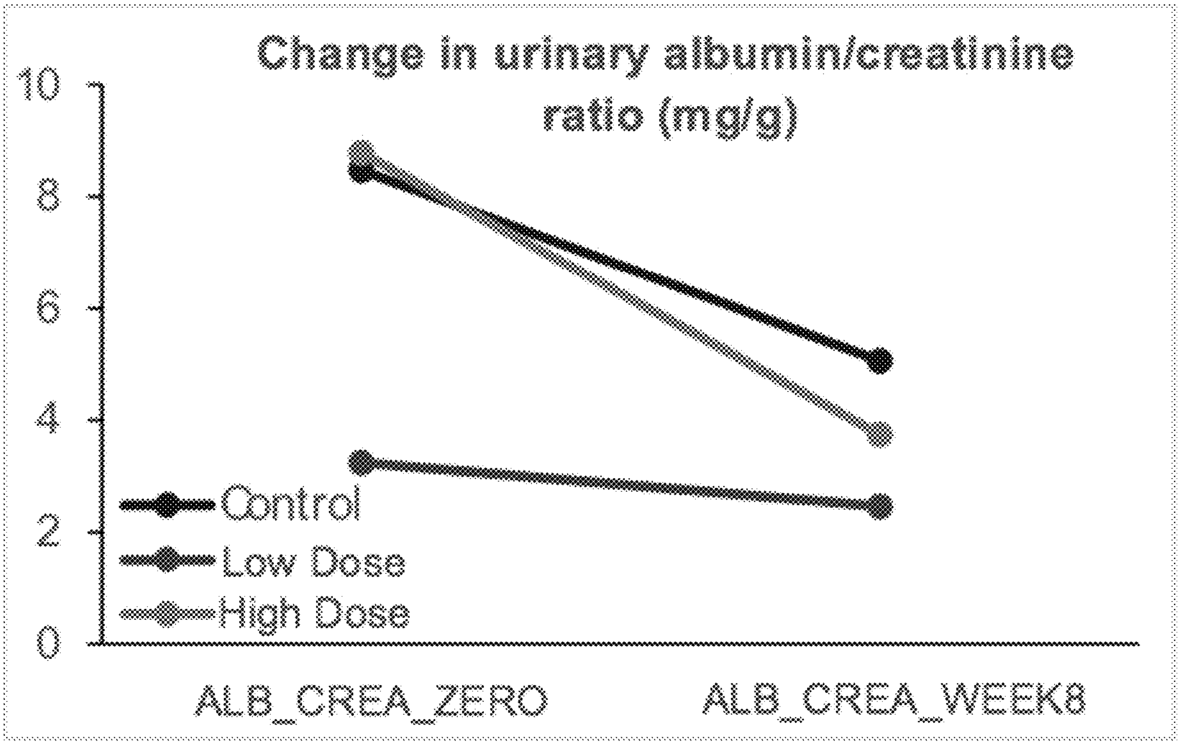
FIG. 11 shows the results of a urinary albumin/creatinine ratio study.

Finally, FIG. 11 teaches the results of the measurement of urinary albumin excretion (UAE), associated with a very early onset of glomerular renal dysfunction. In this way, it is evident that the UAE decreased in the three groups, presenting the greatest decrease in the high dose group (from 8.8 mg/g to 3.8 mg/g). The results also show that the administration of the lipid-based composition with micronutrients of the invention does not exert a renal damage, particularly in glomeruli.

As a consequence, it is possible to conclude that the oral administration of a lipid-based composition with micronutrients according to the invention has no hepatotoxic effect or negatively affects renal function. On the contrary, a positive effect was shown in the reduction of hepatic, hepatobiliary and renal glomerular dysfunction.

Change in Lipid Profile Indicators

Figure 12:
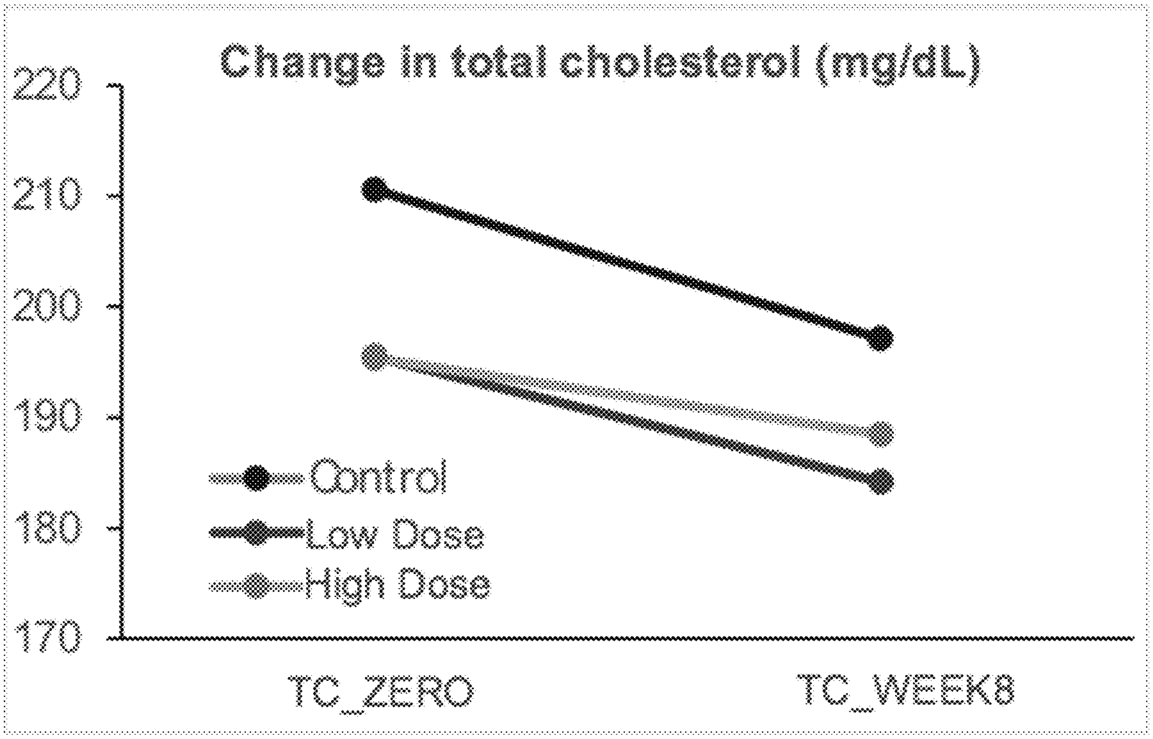
FIG. 12 shows the results of a total cholesterol levels study.

FIG. 12 teaches the results of the measurement of total cholesterol where it is observed that Total Cholesterol decreased in the three groups.

Figure 13:
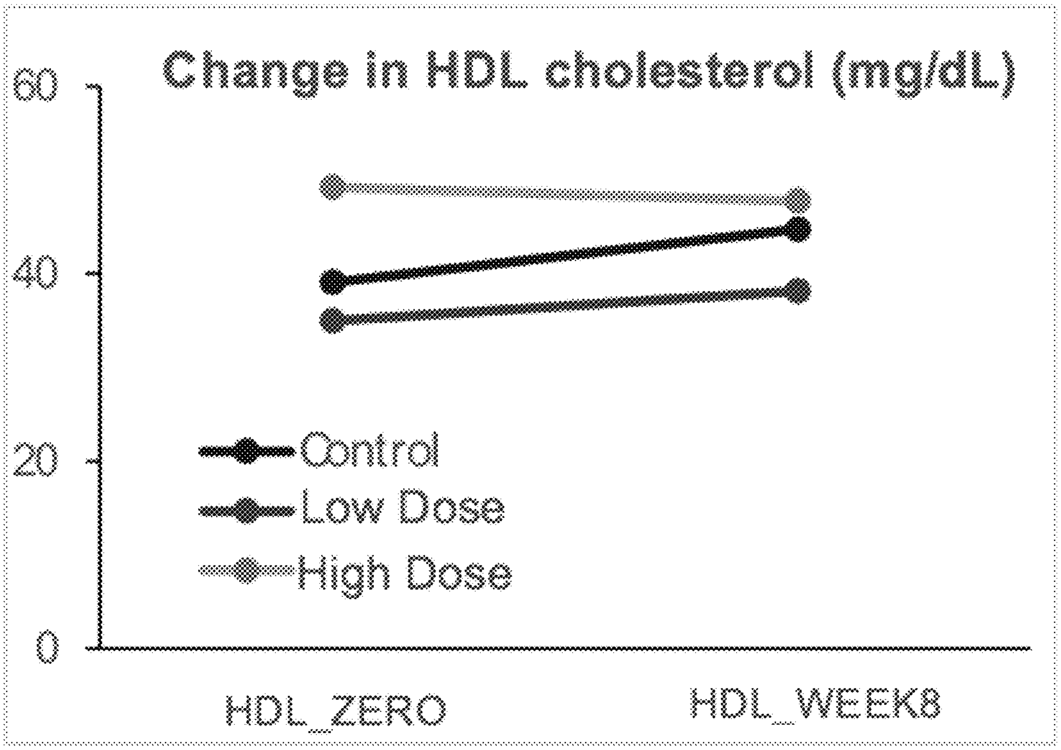
FIG. 13 shows the results of a high density lipoprotein (HDL) levels study.

For its part, in FIG. 13 it is evidenced how HDL cholesterol levels did not considerably change in the high dose group (−1.4 mg/dL), whereas they increased in the low dose (+3.1 mg/dL) and control (+5.7 mg/dL) groups.

Figure 14:
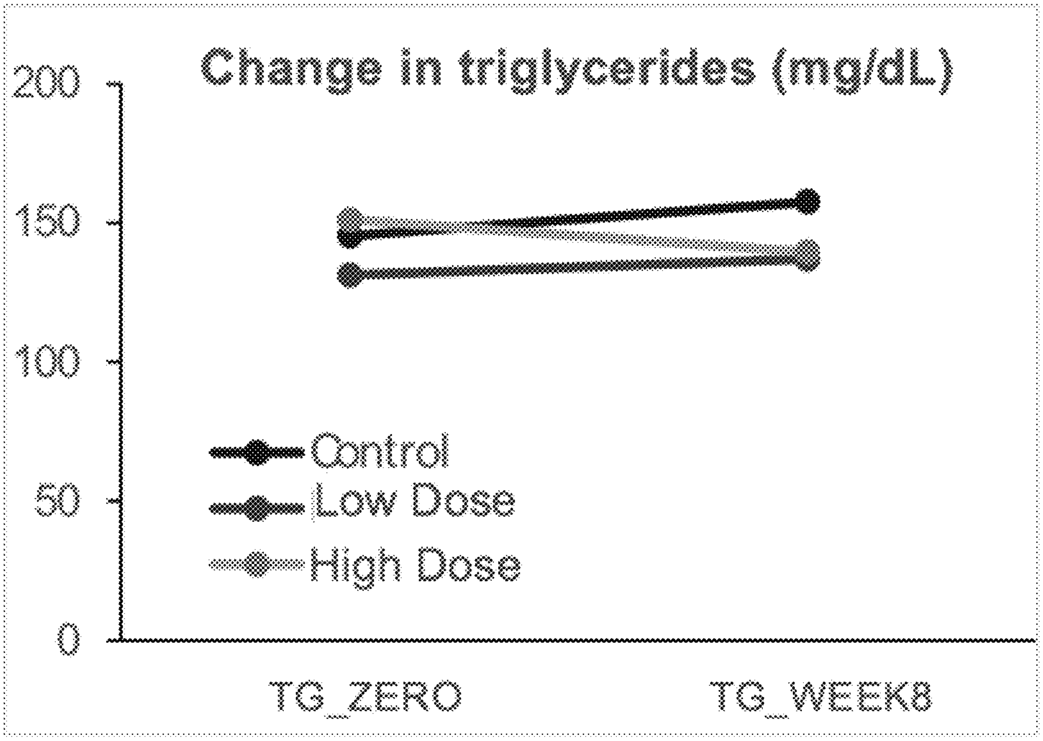
FIG. 14 shows the results of a triglyceride levels study.

On the other hand, FIG. 14 illustrates the results of the determination of triglycerides, which showed great intra- and interindividual variability. Thus, mean triglycerides were elevated in the control group (+12.2 mg/dL) and also in the low-dose group (+5.9 mg/dL), while they decreased in the high-dose group (−11.7 mg/dL).

Figure 15:
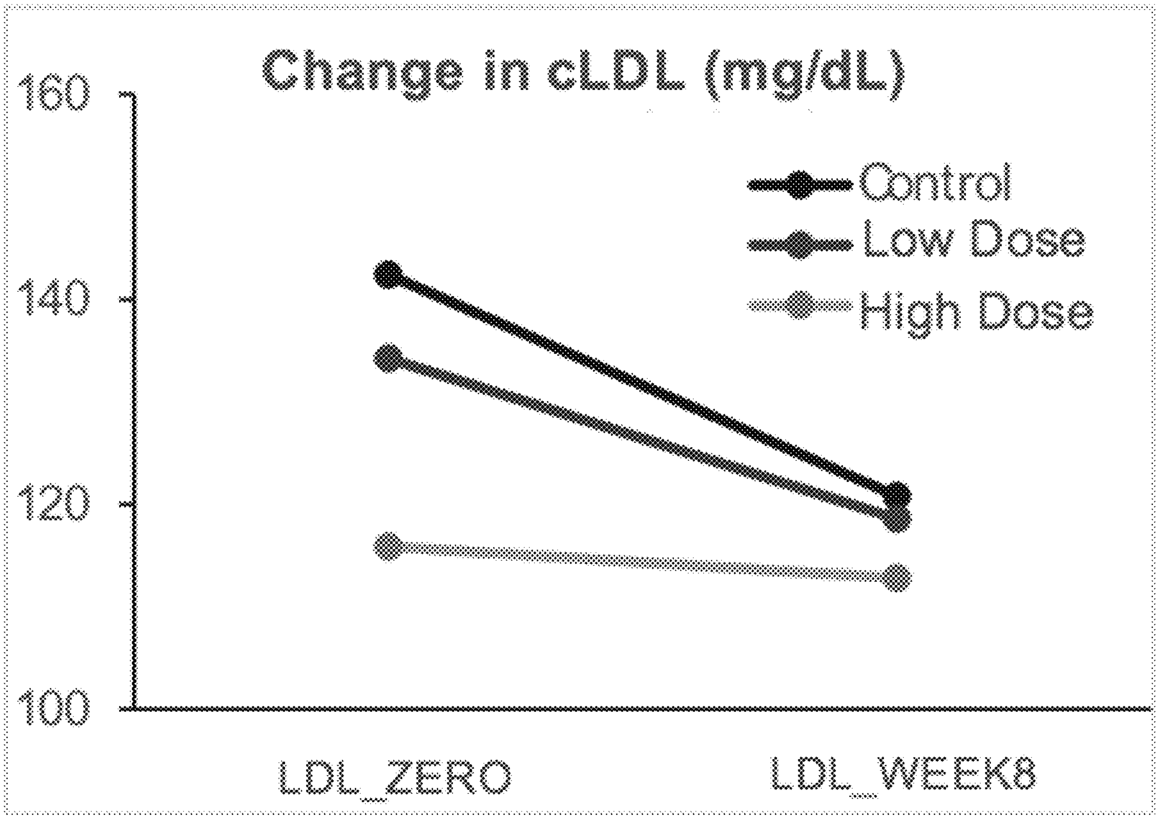
FIG. 15 shows the results of a low density lipoprotein (LDL) levels study.

Finally, FIG. 15 shows that favorable changes were found in the three study groups for LDL-C, the most atherogenic lipid fraction. The decrease was greater in the control group (−21.8 mg/dL) and low dose (−15.6 mg/dL), although the starting point of these two groups is considerably higher.

In this way, the administration of the control and of the lipid-based composition with micronutrients of the invention demonstrate positive effects on the lipid profile of the participants, which is related to the intrinsic properties of sunflower oil, a rich in polyunsaturated fatty acids. However, it is noteworthy that these positive effects, especially in the reduction of LDL cholesterol, speak well about the lipid-based composition with micronutrients of the invention, given the importance of this factor in cardiovascular risk.

In conclusion, the lipid-based composition with micronutrients of the invention clinically demonstrated its ability to impact more than one risk factor in the pathophysiology of type II diabetes mellitus, including: changes in waist circumference, improvement in sensitization and insulin secretion, improved glucose uptake compared to the placebo group, increased hormonal secretion (GLP-1, Leptin, Irisin), decreased low-grade chronic inflammation and reduced hepatobiliary and liver damage.

The lipid-based composition with micronutrients evaluated in this clinical trial offers a highly effective non-pharmacological therapy in the prevention and/or treatment of pre-diabetes and/or hyperglycemia and to favorably modify the course of these metabolic diseases.

The invention claimed is:

1. A lipid-based composition with micronutrients for treating type II diabetes or prediabetes, comprising at least 98 weight percent of naturally occurring lipids including at least one phytosterol and one or more long chain unsaturated fatty acids, wherein the one or more long chain unsaturated fatty acids are selected from a group consisting of pinolenic acid, palmitoleic acid, punicic acid and combinations thereof; at least one natural antioxidant selected from a group consisting of coconut extracts derivatives, canola oil derivatives and combinations thereof, one or more polyphenols of plant origin and at least one chromium compound selected from the group consisting of chromium picolinate, chromium polynicotinate, chromium chloride or mixtures thereof, wherein the one or more long chain unsaturated fatty acids is in a range of between 70 to 90 weight percent which comprises 20 to 30 weight percent pinolenic acid, 30 to 40 weight percent palmitoleic acid and 10 to 20 weight percent punicic acid.

2. The composition of claim 1, wherein the at least one phytosterol is in a range of between 20 to 30 weight percent.

3. The composition of claim 1, wherein the one or more polyphenols of plant origin is in a range of between 0.5 to 5 weight percent.

4. The composition of claim 1, wherein the at least one natural antioxidant is in a range of between 0.3 to 3.0 weight percent.

5. The composition of claim 1, wherein the at least one chromium compound is in a range of between 0.01 to 0.1 weight percent.

6. The composition of claim 5, wherein the at least one chromium compound is selected from inorganic chromium compounds or organic chromium compounds.

7. The composition of claim 1, wherein the naturally occurring lipids including at least one phytosterol and one or more long chain unsaturated fatty acids, the at least one natural antioxidant, and the one or more polyphenols of plant origin comes from natural sources including sea buckthorn oil, pine oil, pomegranate oil, plant phytosterols, turmeric, natural antioxidants derived from coconut extracts, canola oil, or combinations thereof.

8. A method for treating individuals at risk of developing at least one of diabetes or exhibiting pre-diabetes, obesity or overweight, glucose intolerance or insulin resistance, wherein the method comprises administering orally to a human being who need an effective amount per day of a composition according to claim 1.

9. The method of claim 8, wherein the effective amount comprises between 0.5 g to 2 g per dose.

10. The method of claim 8, wherein the effective amount comprises 0.82 g per dose.

11. The method of claim 8, wherein the effective amount comprises 1.64 g per dose.

* * * * *